United States Patent [19]

Jacobson

[11] Patent Number: 5,241,113
[45] Date of Patent: Aug. 31, 1993

[54] PROCESS FOR PRODUCING TRIFLUOROACETYL CHLORIDE

[75] Inventor: Stephen E. Jacobson, Princeton Junction, N.J.

[73] Assignee: E. I. Du Pont de Nemours and Company, Wilmington, Del.

[21] Appl. No.: 945,192

[22] Filed: Sep. 15, 1992

[51] Int. Cl.$^5$ .............................................. C07C 51/31
[52] U.S. Cl. ..................................................... 562/543
[58] Field of Search ......................................... 562/543

[56] References Cited

U.S. PATENT DOCUMENTS 3,883,407  5/1975  Dittman .................... 204/158 R
4,022,824  5/1977  Childs ............................ 260/539 A

FOREIGN PATENT DOCUMENTS 61-39297  9/1986  Japan .

OTHER PUBLICATIONS

Haszeldine and Nyman in *Journal of the Chemical Society*, 1959, p. 420 ff.

*Primary Examiner*—José G. Dees
*Assistant Examiner*—Joseph M. Conrad, III

[57] ABSTRACT

A process for preparing trifluoroacetyl chloride by reacting 1,1-dichloro-2,2,2-trifluoroethane with molecular oxygen over a carbon bed.

4 Claims, No Drawings

PROCESS FOR PRODUCING TRIFLUOROACETYL CHLORIDE

FIELD OF THE INVENTION

This invention relates to a process for preparing trifluoroacetyl chloride by the reaction of 1,1-dichloro-2,2,2-trifluoroethane with molecular oxygen over a carbon bed without the concomitent formation of trifluoroacetic acid.

DESCRIPTION OF THE RELATED ART

Trifluoroacetyl chloride (TFAC) is useful as a starting material for the production of agricultural chemicals or pharmaceuticals, since as the acid chloride it readily reacts with compounds containing amines or alcohols to produce amides or esters, respectively. There are a number of routes in the literature for the production of TFAC each having certain limitations.

For example, a process for the oxidation of 1,1-dichloro-2,2,2-trifluoroethane (HCFC-123) with oxygen in the presence of water is disclosed in U.S. Pat. No. 5,041,647. In that patent it is stated that the water is necessary as a catalyst and that in the absence of water the oxidation of HCFC-123 hardly takes place. "Perfect mixing" is required to prevent local heating, i.e., hot spots. In that process a mixture of TFAC and trifluoroacetic acid (TFAA) is always formed. It is difficult to separate the mixture of water, TFAC, and TFAA, and an object of that patent is the further hydrolysis of the residual TFAC with water at elevated temperatures and pressures to produce TFAA.

Kumai et al., *Reports Res. Lab. Asahi Glass Co., Ltd.*, 41, [1] (1991), studied the reaction of HCFC-123 with oxygen under various conditions. When there was no catalyst, at temperatures up to 450° C. and 50 kg/cm$^2$, either no reaction occurred or there was degradative oxidation to give carbon, carbon dioxide, HCl and HF. They also investigated catalysts such as Pd-Pt/Al$_2$O$_3$, Deacon catalyst, MnO$_2$—CuO/Al$_2$O$_3$, CuO—Cu(II)/-Zeolite Y, at 300°-450° C. with 6-25 seconds contact time. None of these materials catalyzed the conversion of HCFC-123 to TFAC. A mixture of TFAC and TFAA was only formed when the system contained added water and in the liquid phase under pressure. Then by-product TFAA was always present when the TFAC was formed.

SUMMARY OF THE INVENTION

The present invention is a process for preparing TFAC by oxidizing HCFC-123 with molecular oxygen, in the vapor phase at 200°-325° C. over a carbon bed. This invention provides a method for the production of TFAC in which the product can be separated readily from side-reaction products in a highly pure form while minimizing corrosive by-products.

DETAILED DESCRIPTION OF THE INVENTION

This invention to prepare TFAC in an easily purifiable form is carried out by passing a mixture of 1,1- dichloro-2,2,2-trifluoroethane (HCFC-123) and oxygen continuously through a bed of carbon in a hot tube reactor. The exit gases are condensed, and distilled. The desired TFAC is readily separated from the high and low boilers due to the diversity of their boiling points, as shown in Example 1.

The reactor should be made out of materials which will not be seriously corroded by small amounts of reaction by-products such as hydrogen fluoride, as well as small amounts of chlorine and water which can be formed from the reaction of hydrogen chloride and oxygen.

Materials useful for the reactor surfaces include silver, nickel, Hastelloy ®, Inconel ®, and the like. Stainless steel is unsatisfactory as it causes many by-products to be produced and the yield and conversions are lower. Glass is severely etched and therefore not practical. Hastelloy ® C-276 and Inconel ® 600 are the preferred reactor materials since they show minimum corrosion and the yields are consistently higher.

The process is operated at atmospheric pressure, in a temperature range of 200°-325° C. At the lower temperatures the conversion of the starting material is lower and longer reaction times are required. At higher temperatures the amount of by-products increase and the productivity is diminished. The preferred temperature range is 250°-300° C.

As the carbon bed, it is preferred to have activated carbons having a range of surface area from 50 m$^2$/g to 1500 m$^2$/g with the preferred area being >600 m$^2$/g. Various forms of activated carbon may be used, such as granular carbon, coconut shell carbon or carbon molecular sieve. Typical commercially available activated carbons have surface areas ranging from 600-1500 m$^2$/g. Examples of commercially available carbons that are useful in the process of this invention include: North American Carbon Type ® G214D, North American Carbon Type ® G215D, Carbosieve ® G carbon molecular sieve, and Calgon ® PCB carbon. Surprisingly, the presence of metals actually decreases the TFAC yield as exemplified hereinafter.

The reaction to produce TFAC depends upon the contact time and the temperature. The longer the contact time the greater the conversion of the starting material HCFC-123. In addition the longer contact time at elevated temperatures results in increased levels of decomposition products. Thus there is a balance between contact time and temperature to give optimum results. Contact times of 1second to 2 minutes have been shown to produce the desired product with the preferred time range being 10 seconds to 60 seconds.

EXAMPLES

The following examples serve to illustrate the invention, but are not intended to limit the scope of the invention.

In the examples below the following abbreviations are used. CFC-113a is 1,1,1-trichloro-2,2,2-trifluoroethane, CFC-13 is chlorotrifluoromethane, CFC-23 is trifluoromethane, CFC-114a is CF$_3$CFCl$_2$.

All analyses in the following examples were by gas chromatography using a Hewlett-Packard Series II 5890 instrument coupled with a 3393A integrator. A 105 m×0.32 mm RTX-1 (Restek Corp., Bellefonte, Pa.) capillary column was used with a thermal conductivity detector. A temperature program of 40° C. (15 min hold), heating 16° C./min to 200° C. (10 minute hold), and heating 50° C./min to 250° C. (10 minute hold) was employed.

EXAMPLE 1

A 13"×⅜" Hastelloy ® C-276 tube was packed with 25 cc (9.8 g) of North American Carbon Type ® G214D. The tube was heated to 275° C. under a nitrogen atmosphere. A mixture of HCFC-123 at 0.10 cc/min and molecular oxygen at 25 cc/min was heated to 275° C. at atmospheric pressure, and continuously fed over the carbon bed. Contact time was 16 seconds. The reaction was monitored by gas chromatography samples of the exit vapor. The analyses indicated a 100% conversion of HCFC-123 to TFAC (39%), CFC-113a (31%), CFC-13 (19%), and CFC-23 (8%). The oxidation products were readily condensed in a dry ice trap. The condensed liquid could readily be distilled and the products separated in a ten plate Oldershaw column. The low boilers CFC-13 (bp $-84°$ C.) and CFC-23 (bp $-81°$ C.) appeared in the forecut, the desired TFAC (bp $-27°$ C.) is removed in >99% purity in the next cut and the residual CFC-113a (bp 46° C.) remained in the still.

EXAMPLE 2

North American Carbon® G215D was packed in the same reactor as described in Example 1. A preheated mixture of HCFC-123 and molecular oxygen was fed. at the same flow rates as in Example 1 over the carbon bed for three hours at 275° C. The analyses indicated a 100% conversion of HCFC-123 to TFAC (35%), CFC-113A (37%), and CFC-13 (26%).

EXAMPLE 3

Carbosieve® G carbon molecular sieve (12.5 g) was packed into the reactor. A preheated mixture of HCFC-123 and molecular oxygen was fed at the same flow rates as Example 1 over the carbon molecular sieve bed for 100 minutes at 300° C. The analyses indicated a 100% HCFC-123 conversion to TFAC (45%), CFC-113A (28%), CFC-13 (25%), and CFC-23 (2%).

EXAMPLE 4

Using the same catalyst in Example 3, a premixed sample of HCFC-123 (0.2 cc/min) and oxygen (50 cc/min) at 300° C. was fed for 100 minutes (contact time 4 seconds). The analyses indicated a 71% HCFC-123 conversion to TFAC (56%), CFC-113A (26%), CFC-13 (16%), and CFC-23 (2%).

EXAMPLE 5

Calgon® PCB carbon (12.5 cc) was packed into the reactor described in Example 1. A preheated mixture of HCFC-123 (0.1 cc/min) and molecular oxygen (25 cc/min) was fed over the carbon bed at 275° C. for 200 minutes (contact time 8 seconds). The analyses indicated a 91% conversion of HCFC-123 to TFAC (29%), CFC-113A (37%), and CFC-23 (7%).

Surprisingly the presence of metals actually decreased the TFAC yield, as shown by the next two comparative examples.

COMPARATIVE EXAMPLE 6

$CuCl_2$ (5%) on Calgon PCB carbon (25 cc) was packed into the reactor. A preheated mixture of HCFC-123 (0.1 cc/min) and oxygen (23 cc/min) was preheated and fed over the carbon bed for 100 minutes at 200° C. (contact time 20 seconds). The analysis indicated an 83% HCFC-123 conversion to TFAC (7%), CFC-13 (39%), CFC-113A (13%), and carbon dioxide (21%).

COMPARATIVE EXAMPLE 7

An identical run to Example 6 at 230° C. for 100 minutes at 230° C. gave TFAC (1%), CFC-13 (53%), CFC-113a (18%), CFC-23 (1%), and carbon dioxide (25%). Contact time was 18 seconds to give 100% conversion of HCFC-123.

What is claimed is:

1. A process for the continuous production of trifluoroacetyl chloride which comprises passing a mixture of 1,1-dichloro-2,2,2-trifluoroethane and molecular oxygen over a carbon bed maintained at a temperature from 200°–325° C.

2. The process of claim 1 wherein the carbon bed is activated carbon having a surface area from 50 m$^2$/g to 1500 m$^2$/g.

3. The process of claim 2 wherein the activated carbon is selected from the group consisting of granular carbon, coconut shell carbon, or carbon molecular sieve.

4. The process of claim 1 wherein the process is in the vapor phase.

* * * * *